US006602915B2

(12) United States Patent
Uhrich

(10) Patent No.: US 6,602,915 B2
(45) Date of Patent: Aug. 5, 2003

(54) THERAPEUTIC AZO-COMPOUNDS FOR DRUG DELIVERY

(75) Inventor: Kathryn E. Uhrich, Hoboken, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/917,595

(22) Filed: Jul. 27, 2001

(65) Prior Publication Data
US 2002/0071821 A1 Jun. 13, 2002

Related U.S. Application Data

(60) Provisional application No. 60/220,998, filed on Jul. 27, 2000.

(51) Int. Cl.[7] .................. A61K 47/30; A61K 47/31; A61K 47/34; A61K 31/74
(52) U.S. Cl. .................. 514/772.2; 424/78.08
(58) Field of Search .................. 514/772.2; 424/428, 424/427, 78.08, 409, 420

(56) References Cited

U.S. PATENT DOCUMENTS

| 4,062,855 A | 12/1977 | Allan et al. ............ 260/295 PA |
| 4,126,445 A | 11/1978 | Allan et al. .................. 71/94 |
| 4,298,595 A | 11/1981 | Parkinson et al. ............ 424/78 |
| 4,684,620 A | 8/1987 | Hruby et al. .................. 514/11 |
| 4,757,128 A | 7/1988 | Domb et al. .................. 528/271 |
| 4,792,598 A | 12/1988 | Ziegast ..................... 528/206 |
| 4,857,311 A | 8/1989 | Domb et al. .................. 424/78 |
| 4,868,274 A | 9/1989 | Gupta et al. .................. 528/206 |
| 4,886,870 A | 12/1989 | D'Amore et al. ............ 528/206 |
| 4,888,176 A | 12/1989 | Langer et al. .............. 424/428 |
| 4,891,225 A | 1/1990 | Langer et al. .............. 424/428 |
| 4,906,474 A | 3/1990 | Langer et al. .............. 424/428 |
| 4,997,904 A | 3/1991 | Domb ..................... 528/206 |
| 4,999,417 A | 3/1991 | Domb ..................... 528/271 |
| 5,082,925 A | 1/1992 | Shalaby et al. ............ 528/354 |
| 5,175,235 A | 12/1992 | Domb et al. .................. 528/271 |
| 5,259,968 A | 11/1993 | Emert et al. ............ 252/51.5 A |
| 5,264,540 A | 11/1993 | Cooper et al. .............. 528/272 |
| 5,498,729 A | 3/1996 | Domb ..................... 548/500 |
| 5,514,764 A | 5/1996 | Frechet et al. .............. 528/10 |
| 5,518,730 A | 5/1996 | Fuisz ..................... 424/426 |
| 5,545,409 A | 8/1996 | Laurencin et al. .......... 424/426 |
| 5,629,009 A | 5/1997 | Laurencin et al. .......... 424/426 |
| 5,889,028 A * | 3/1999 | Sandborn et al. ............ 514/343 |
| 5,902,599 A | 5/1999 | Anseth et al. .............. 424/426 |
| 5,942,252 A | 8/1999 | Tice et al. ................. 424/501 |
| 6,071,530 A | 6/2000 | Polson et al. .............. 424/426 |
| 6,153,212 A | 11/2000 | Mao et al. .................. 424/426 |

FOREIGN PATENT DOCUMENTS

| DE | 288311 | 3/1991 | .......... A01N/25/10 |
| DE | 288387 | 3/1991 | ........... C08G/67/04 |
| EP | 0246341 | 11/1987 | .......... A61L/27/00 |
| NL | 9000237 | 8/1991 | .......... A61K/31/60 |
| WO | WO-91/09831 | 7/1991 | ......... C07C/69/035 |
| WO | WO-97/39738 | 10/1997 | ............ A61K/9/16 |
| WO | WO-98/36013 | 8/1998 | ........... C08G/64/00 |
| WO | WO-99/12990 | 3/1999 | ........... C08G/63/00 |
| WO | WO-99/29885 | 6/1999 | ............. C12P/1/00 |
| WO | WO-01/28492 | 4/2001 | |
| WO | WO-02/09767 | 2/2002 | .......... A61K/47/48 |
| WO | WO-02/09768 | 2/2002 | .......... A61K/47/48 |
| WO | WO-02/09769 | 2/2002 | .......... A61K/47/48 |

OTHER PUBLICATIONS

Erdmann et al. ("Polymeric Prodrugs: Novel Polymers with bioactive components", in Tailored Polymeric Materials for Controlled Delivery Systems, McCulloch et al. edited, ACS Symposium Series 709, 1998, pp. 83–91).*

Anastasiou et al. ("Synthesis of Novel, Degradable Polyanhydrides Containing Para–Aminosalicylic Acid as Drug Delivery Devices for Tubeculosis Treatment". Polymer Preprints, 41 (2), Aug. 2000, pp. 1366 and 1367).*

Anastasiou, T.,et al. ,"Synthesis of Novel, Degradable Polyanhydrides Containing Para–Aminosalicylic Acid as Drug Delivery Devices for Tubeculosis Treatment", *Polymer Preprints, 41*(2), (2000),p. 1366.

Attawia, M.A. , "Biocompatibility Testing of Poly(anhydride–co–imides) Containing Pyromellitylimidoalanine", *The 21st Annual Meeting of the Society for Biomaterials,* Abstract(1994),p. 222.

Attawia, M.A., "Regional drug delivery with radiation for the treatment of Ewing's sarcoma—In vitro development of a taxol release system", *Journal of Controlled Release, 71,* (2001), pp. 193–202.

Brown, J.P.,et al. ,"A Polymeric Drug for Treatment of Inflammatory Bowel Disease", *J. Med. Chem., 26,* (1983), 1300–1307.

Chatterjee, R., et al., "Mechanism for the Increase in Solubility of Deoxyhemoglobin S Due to Cross–Linking the beta Chains between Lysine–82beta1 and Lysine–82beta2", *Biochemistry, 21,* (1982),5901–5909.

Conix, A.,et al. , "New High–Melting Fibre–Forming Polymers", *Die Markomolekulare Chemie, XXIV,* (1957), 76–78.

Davaran, S.,et al. ,"Release of 5–amino Salicylic Acid from Acrylic Type Polymeric Prodrugs Designed for Colon–specific Drug Delivery", *Journal of Controlled Release, 58,* (1999),279–287.

(List continued on next page.)

Primary Examiner—Thurman K. Page
Assistant Examiner—Blessing Fubara
(74) Attorney, Agent, or Firm—Schwegman, Lundberg, Woessner & Kluth, P.A.

(57) ABSTRACT

Polyazo compounds, which include low molecular weight drugs having a carboxylic acid group and an amine, thiol, alcohol or phenol group within their structure, formed into polymeric drug delivery systems are provided. Also provided are methods of producing polymeric drug delivery systems having these polyazo compounds as well as methods of administering low molecular weight drugs to a host via the polymeric drug delivery systems.

36 Claims, No Drawings

OTHER PUBLICATIONS

Erdman, "Polymer Prodrugs with Pharmaceutically Active Degradation Products", *Polymer Preprints, 38 (2)*, (1997), 570–571.

IBIM, S., "Controlled Release Based on Poly(anhydride–co–imides)", *Proc. Intern. Symp. Control. Rel. Bioact. Mater., 22*, (1995),2 pgs.

IBIM, S.E., "Preliminary In Vivo Report on the Osteocompatibility of Poly(anhydride–co–imides) evaluated in a Tibial Model", *App. Biomater., 43 (4)*, (1998),pp. 374–379.

Jiang, H.L. ,et al. ,"Synthesis, Characterization and In Vitro Degradation of a New Family of Alternate Poly(ester–anhydrides) Based on Aliphatic and Aromatic Diacids", *Biomaterials, 22*, (2001),211–218.

Laurencin, C.T.,"The Biocompatibility of Poly(anhydride–co–imides): High Strength Polymers for Controlled Drug Delivery", *Proc. 24th Int'l Symp. Control. Rel. Bioact. Mater.*, (1997),pp. 973–974.

Laurencin, C.T.,"The Bone Biocompatibility of Poly(anhydride–co–imides)—A new generation degradable Polymer for Orthopedic Applications", *41st Annual Meeting of the Orthopedic Research Society, Orlando, FL*, (1995),pp. 143–224.

Laurencin, C.T.,"The Controlled Delivery of Radiosensitizers: Taxol Treatment for Ewing Sarcoma", *Proc. of the 25th Int'l Symp. Control. Rel. Bioact. Mater.*, (1998),pp. 236–237.

Schacht, E.,et al. ,"Polymers for Colon Specific Drug Delivery", *Journal of Controlled Release, 39*, (1996),327–338.

Shen, E., "Morphological Characterization of Erodible Polymer Carriers for Drug Release", *Proc. 26th Int'l Symp. Control. Rel. Bioact. Mater.*, (1999),pp. 717–718.

Uhrich, K.E.,"Chemical Changes during in vivo degradation of poly(anhydride–imide) matrices", *Biomaterials, 19*, (1998),pp. 2045–2050.

Uhrich, K.E.,"Degradation of poly(anhydride–co–imides): Novel Polymers for Orthopedic Applications", *Mat. Res. Soc. Symp. Proc., 394*, (1995),pp. 41–46.

Anastasiou, T..J. ,"Novel Polyanhydrides with Enhanced Thermal and Solubility Properties", *Macromolecules, 33 (17)*, (2000),pp. 6217–6221.

Anastasiou, T..J. ,"Novel, Degradable Polyanhydrides", *25th Annual Meeting Transactions of the Society for Biomaterials*, Abstract,(1999),p. 79.

Anastasiou, T..J. ,"Synthesis of Novel, Degradable Polyanhydrides Containing Para–Aminosalicylic Acid as Drug Delivery Devices for Tuberculosis Treatment", *Polymer Preprints*, 41 (2), (Aug. 2000),pp. 1366–1367.

Beaton, M..L. ,"Synthesis of a novel poly(anhydride–ester)", *The Rutgers Scholar—An Electronic Bulletin of Undergraduate Research, 3*, www.rutgersscholar.rutgers.edu/volume03/beatuhri/beatuhri.html,(2001),7 pgs.

Bedell, C.,"Processing and Hydrolytic Degradation of Aromatic, Ortho–Substituted Polyanhydrides", *Journal of Applied Polymer Science, 80*, (2001),pp. 32–38.

Campo, C..J. ,"Polyanhydrides: the effects of ring substitution changes on polymer properties", *Polymer Bulletin, 42*, (1999),pp. 61–68.

Chafi, N.., "Dosage Form with Salicylic Acid Attached to the Polyanhydride Polymer Dispersed in an Eudragit Matrix", *International Journal of Pharmaceutics, 52*, (1989),pp. 203–211.

Conix, A.., "Aromatic Polyanhydrides, a New Class of High Melting Fiber–Forming Polymers", *Journal of Polymer Science, XXIX*, (1958),pp. 343–353.

Conix, A.., "New High–Melting Fibre–Forming Polymers", *Die Makromolekulare Chemie, XXIV*, (1957),pp. 76–78.

Conix, A.., "Poly[1,3–bis(p–carboxyphenoxy)–Propane anhydride]", *Macromolecular Synthesis*, 2, (1996), pp.95–99.

Domb, A..J. ,"Synthesis and Characterization of Biodegradable Aromatic Anhydride Copolymers", *Macromolecules, 25*, (1992),pp. 12–17.

Dukovic, G.,"Novel degradable poly(anhydride–esters) for controlled drug release", *The Rutgers Scholar—An Electronic Bulletin of Undergraduate Research, 1*, http://rutgersscholar.rutgers.edu/colume01/uhriduko/uhriduko.html, (1999),10 pgs.

Erdman, L..,et al. ,"Polymer Prodrugs with Pharmaceutically Active Degradation Products", *Polymer Preprints, 38 (2)*, (1997),pp. 570–571.

Erdmann, L..,"Chapter 5: Polymeric Prodrugs: Novel Polymers with Bioactive Components", *In: Tailored Polymeric Materials for Controlled Delivery Systems*, I. McCulloch, et al., (Editors), ACS Symposium Series 709, American Chemical Society: Washington, D.C.,(1998),pp. 83–91.

Erdmann, L.,"Degradable poly(anhydride ester) implants: effects of localized salicylic acid release on bone", *Biomaterials, 21*, (2000),pp. 2507–2512.

Erdmann, L.., "Polymeric Prodrugs: Novel Polymers for Delivery of Salicyclic Acid", *Annals of Biomedical Engineering, 26 (Suppl. 1)*, Abstract No. PB.26, Annual Fall Meeting,(1998),p. S–124.

Erdmann, L..,"Polymeric Salicylic Acid: In Vitro and In Vivo Degradation", *Polymer Preprints, 39 (2)*, (1998),p. 224–225.

Erdmann, L..,"Synthesis and Characterization of a Polymeric Prodrug", *Proceedings of the American Chemical Society Division of Polymeric Materials: Science and Engineering, 78*, Abstract of Spring Meeting, Dallas, TX,(1998), p. 194.

Erdmann, L.., "Synthesis and degradation characteristics of salicylic acid–derived poly(anhydrid–esters)", *Biomaterials, 21*, (2000),pp. 1941–1946.

Giammona, G..,"Polymeric Prodrugs alpha beta poly–hydroxyethyl–d1–aspartamide as macromolecular carrier for some non–steroidal anti–inflammatory agents", *Abstract for Database BIOSIS Online, Bioscience Information Service, Philadelphia, PA*, Original Publication from the International Journal of Pharmaceutics (Amsterdam), (1989), 1 pg.

Gouin, S..,et al. ,"New Polyanhydrides Made From a Bile Acid Dimer and Sebacic Acid: Synthesis, Characterization, and Degradation", *Macromolecules, 33*, (2000),pp. 5379–5383.

IBIM, S.M. ,"Poly(anhydride–co–imides): In Vivo Biocompatibility in a rat model", *Biomaterials, 19*, (1998),pp. 941–951.

Krogh–Jespersen, E.,"Synthesis of a Novel Aromatic Polyanhydride Containing Aminosalicylic Acid", *Polymer Preprints, 41 (1)*, (2000),pp. 1048–1049.

Langer, R..,"New Methods of Drug Delivery", *Science, 249*, (Sep. 1990),pp.1527–1533.

Macedo, B..,et al. ,"The in vivo Response to a Bioactive Biodegadable Polymer", *Journal of Dental Research, 78*, Abstract No. 2827,(1999),. 459.

Macedo, B.,"the In Vivo Response to Bioactive Polyanhydride Monofilament", *Journal of Dental Research, 79 (Abstract No. 3872)*, (2000),p. 627.

Pinther, P..,"Synthesis of Polyanhydrides Containing Ester Groups", *Makromol. Chem., Rapid Commun., 11*, (1990),pp. 403–408.

Seidel, J.O. ,"Erosion of Poly(anhydride–co–imides): A Preliminary Mechanistic Study", *J. Appl. Polym. Sci., 62(8)*, (1996),pp. 1277–1283.

Uhrich, K.E. ,"In Vitro Degradation Characteristics of Poly(anhydride–imides) Containing Pyromellitylimidoalanine", *J. Appl. Polymer Sci., Part A, Polym. Chem., 34 (7)*, (1996), pp. 1261–1269.

Uhrich, K.E. ,"In Vitro Degradation Characteristics of Poly(anhydride–imides) Containing trimellitylimidoglycine", *J. Appl. Polymer. Sci., 63 (11)*, (1997),pp. 1401–1411.

Uhrich, K.E. ,"Poly(anhydride–ester) Degradation: Mechanical Changes and Correlation to Antibiotic Release", *American Chemical Society, Abstracts of Papers, Part 2, Abstract No. 121*, 2221st ACS National Meeting, San Diego, CA,(2001), 1 pg.

Uhrich, K.E. ,"Synthesis and Characterization of Degradable poly(anhydride–co–imides)", *Macromolecules, 28 (7)*, (1995), pp. 2184–2193.

Uhrich, K.E. ,"Synthesis and Characterization of poly(anhydride–co–imides): Solution Polycondensation of Biodegradable Polymers Derived from Amino Acids", *Proc. of the American Chemical Society, Division of Polymeric Materials: Science and Engineering, 70*, Spring Meeting, San Diego, CA,(1994),pp. 239–240.

Uhrich, K.E. ,"Synthesis of Aminosalicylate–based polyanhydride Prodrugs: Esters, Amides, and Azos", *American Chemical Society, Abstracts of Papers, Part 2, Abstract No. 407*, 222nd ACS National Meeting, Chicago, IL,(2001),1 pg.

* cited by examiner

THERAPEUTIC AZO-COMPOUNDS FOR DRUG DELIVERY

PRIORITY OF INVENTION

This application claims priority from U.S. Provisional Patent Application No. 60/220,998, filed Jul. 27, 2000), which is incorporated herein by reference.

BACKGROUND OF THE INVENTION

5-Aminosalicylic acid (5-ASA) is the active component of a commonly used treatment for inflammatory bowel disease (IBD) and Crohn's disease treatment. 5-ASA drug is typically linked via an azo bond to a carrier that allows for targeted drug release exclusively in the large intestine where the azo bond is cleaved by the indigenous bacteria. However, the carrier molecule for this component is associated with several side effects such as nausea and vomiting, rash, or other severe toxic reactions.

4-Aminosalicylic acid (4-ASA) has shown promise in the treatment of inflammatory bowel disease as well as tuberculosis. However, this drug causes several objectionable side effects. Some of the less common side effects are hepatitis, hypokalemia, acute renal failure, mild hypoprothrombinemia, hemolytic anaemia and thrombocytopenia. Patients can also develop hypersensitivity and hypothyroidism and goiter. The side effects that makes this drug intolerable to patients, however, are the gastrointestinal reactions. 4-ASA is a gastrointestinal irritant which frequently causes symptoms of anorexia, nausea, vomiting, and diarrhea. The diarrhea can be severe enough to cause steatorrhea, malabsorption, secondary folic acid deficiency and megaloblastic anemia.

Accordingly, attempts have been made to prepare formulations which alleviate these side effects. Several formulations have been created which include enteric-coated tablets and granules, solutions, and suspensions, as well as chemically modified forms such as complexes with resin and ascorbic acid, phenyl esters, and benzoyl amides. Several polymeric drugs incorporating 4-ASA based on either dialdehyde starch/oxidized cellulose, poly(vinyl alcohol), or polyacrylate backbones have also been prepared.

In the present invention, drugs are incorporated into polymeric systems to furnish a polyazo compound. Using these polymeric drug delivery systems, targeted and temporal drug delivery can be achieved, without unwanted side effects of the current formulations.

SUMMARY OF THE INVENTION

Polymeric polyazo compounds which degrade into useful biologically active compounds have now been developed. Accordingly, the invention provides a polymer of the invention which comprises a backbone, wherein the backbone has an azo linkage, and wherein the backbone has one or more groups that will yield a biologically active compound upon hydrolysis and cleavage of the azo-bond of the polymer.

The invention also provides a pharmaceutical composition comprising a polymer of the invention and a pharmaceutically acceptable carrier.

The invention also provides a therapeutic method for treating a disease in an animal comprising administering to an animal in need of such therapy, an effective amount of a polymer of the invention.

The invention also provides a method of delivering a biologically active compound to a host comprising administering to the host a biocompatible and biodegradable polymer of the invention, which degrades into the biologically active compound.

The invention provides a polymer of the invention for use in medical therapy, as well as the use of a polymer of the invention for the manufacture of a medicament useful for the treatment of a disease in a mammal, such as a human.

The invention also provides a therapeutic method for treating inflammatory bowel disease, cancer, or a brain tumor comprising administering to a mammal in need of such therapy, an effective amount of a polymer of any one of formula (III), (IV) or (V), as described herein.

The invention also provides a therapeutic method for producing an anti-infective effect in an animal comprising administering to an animal in need of such therapy, an effective amount of a polymer of any one of formula (III), (IV) or (V), as described herein.

The invention also provides a therapeutic method for treating cancer comprising administering to an animal in need of such therapy, an effective amount of a polymer of any one of formula (III), (IV) or (V), as described herein.

The invention also provides processes and intermediates disclosed herein that are useful for preparing a polymer of the invention.

DETAILED DESCRIPTION OF THE INVENTION

Definitions

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$–$C_6$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term anhydride linkage means —C(=O)—O—(O=)C—, term ester linkage means —OC(=O)— or —C(=O)O—; the term thioester linkage means —SC(=O)— or —C(=O)S—; and the term amide linkage means —N(R)C(=O)— or —C(=O)N(R)—, wherein each R is a suitable organic radical, such as, for example, hydrogen, ($C_{1-6}$)alkyl, ($C_3$–$C_6$)cycloalkyl, ($C_3$–$C_6$) cycloalkyl($C_1$–$C_6$)alkyl, aryl, heteroaryl, aryl($C_1$–$C_6$)alkyl, or heteroaryl($C_1$–$C_6$)alkyl.

The term "amino acid," comprises the residues of the natural amino acids (e.g. Ala, Arg, Asn, Asp, Cys, Glu, Gln, Gly, His, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_{1-6}$)alkyl, phenyl or benzyl ester or amide; or as an α-methylbenzyl amide). Other suitable amino and carboxy protecting groups are known to those skilled in the art (See for example, Greene, T. W.; Wutz, P. G. M. "Protecting Groups In Organic Synthesis" second edition, 1991, New York, John Wiley & sons, Inc., and references cited therein).

The term "host" includes animals and plants.

The term "peptide" describes a sequence of 2 to 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

Polymers of the Invention

The biocompatible, biodegradable polyazo compounds of the invention are useful in a variety of applications where delivery of a biologically active compound (active agent) to the large intestine is desired.

The polymers of the invention may be prepared in accordance with methods commonly employed in the field of synthetic polymers to produce a variety of useful products with valuable physical and chemical properties. The polymers can be readily processed into tablets, coatings, and microspheres for delivery of the active agent.

Polymers of the present invention can also be incorporated into oral or rectal formulations.

Although the invention provides homopolymers that are prepared from suitably functionalized biologically active compounds, Applicant has discovered that the mechanical and hydrolytic properties of polymers comprising one or more biologically active compounds can be controlled by incorporating a linking group (L) into the polymer backbone.

Preferably, the polymers of the invention comprise backbones wherein biologically active compounds and linker groups are bonded together through anhydride linkages, ester linkages, thioester linkages, amide linkages, or a mixture thereof. Due to the presence of the linking groups, the polymers can be hydrolyzed under physiological conditions to provide the azo-compounds containing the active agent. Thus, the polymers of the invention can be particularly useful as a controlled release source for a biologically active compound, or as a medium for the localized delivery of a biologically active compound, to the lower intestine. For example, the polymers of the invention can be used for the localized delivery of a therapeutic agent for treatment of intestinal conditions such as inflammatory bowel disease and Crohn's disease or for the treatment of tuberculosis in a patient which comprises orally administering to the patient a polymeric drug delivery system comprising a poly(azo-anhydride) of 5-ASA or 4-ASA.

Azo-polymers prepared in accordance with the present invention have average molecular weights of about 1500 daltons up to about 100,000 daltons, calculated by Gel Permeation Chromatography (GPC) relative to narrow molecular weight polystyrene standards. Preferred aromatic polyanhydrides have average molecular weights of about 1500 daltons, up to about 50,000 daltons calculated by Gel Permeation Chromatography (GPC) relative to narrow molecular weight polystyrene standards. Preferred azo-polymers have average molecular weights of about 1500 Daltons, up to about 35,000 Daltons.

In the chemically linked azo active agents of the polymeric drug delivery system, drug release becomes dependant upon pH as well as bacterial degradation. For example, using the polyazo compounds of the invention, a polymeric form of a current Crohn's disease drug, olsalazine, can be prepared which will undergo hydrolysis and bacterial degradation (azo cleavage) to release the drug. In this embodiment, the only active degradation product is the free drug, 5-ASA. Thus, side effects associated with current 5-ASA preparations are eliminated. In addition, the majority, if not all, of the drug is released at the target (large intestine) due to pH and indigenous flora. Further, polyanhydride linkages have been associated with intestinal mucosal adhesion, which may impart a beneficial temporal control aspect to these materials as well.

Another example is 4-ASA. 4-ASA is associated with a low biological half-life, thus daily dosages can be on the order of ten to fifteen grams per day. By incorporating 4-ASA into a polymeric azo compound, specifically a poly (azo-anhydride) compound, the drug can be released gradually through cleavage of the azo bond by intestinal bacteria as it passes through the alimentary canal. In this way, it is expected that 4-ASA will gradually be absorbed into the bloodstream. Thus, 4-ASA serum levels can be maintained and stabilized over time. This could eliminate the need for repeated doses. 4-ASA is also being investigated as a treatment for inflammatory bowel disease in addition to its use as a tuberculostatic drug. Thus, polymeric drug delivery systems comprising 4-ASA may have uses that parallel those of the 5-ASA polymers described above.

Biologically Active Compounds

The term "biologically active compound" includes therapeutic agents that provide a therapeutically desirable effect when administered to an animal (e.g., a mammal, such as a human). Biologically active compounds that can be incorporated into the polymers of the invention possess at least two functional groups. One group can form the azo group and the other that can each be incorporated into an anhydride, ester, thioester, or amide linkage of a polymer (as discussed in detail below), such that, upon hydrolysis of the polymer, the therapeutic agent is obtained. These groups can independently be a hydroxy group (—OH), a mercapto group (—SH), an amine group (—NHR), or a carboxylic acid (—COOH).

The biologically active compounds can also comprise other functional groups (including hydroxy groups, mercapto groups, amine groups, and carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer). Lists of therapeutic agents can be found, for example, in: Physicians' Desk Reference, 55 ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12 ed., 1996, Merck & Co., Inc., Whitehouse Station, N.J. One skilled in the art can readily select therapeutic agents that possess the necessary functional groups for incorporation into the polymers of the invention from these lists.

Therapeutic agents that can be incorporated into the polymers of the invention include suitably functionalized analgesics, anesthetics, anti-convulsants, anti-diabetic agents, anti-fibrotic agents, anti-infectives, anti-bacterials, anti-fungals, anti-thrombotics, anti-neoplastics, cardioprotective agents, cardiovascular agents, central nervous system stimulants, cholinesterase inhibitors, contraceptives, dopamine receptor agonists, erectile dysfunction agents, fertility agents, gastrointestinal agents, gout agents, hormones, immunomodulators, immunosuppressives, migraine agents, motion sickness agents, muscle relaxants, non-steriodal anti-inflammatory drugs, nucleoside analogs, obesity agents, ophthalmic agents, osteoporosis agents, parasympatholytics, parasympathommetics, prostaglandins, psychotherapeutic agents, respiratory agents, sedatives, hypnotics, smoking cessation agents, sympatholytics, urinary tract agents, and vasodilators (see Physician's Desk Reference, 55 ed., 2001, Medical Economics Company, Inc., Montvale, N.J., pages 201–202).

Examples of anti-bacterial compounds suitable for use in the present invention include, but are not limited to 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apramycin, arbekacin, aspoxicillin, aztreonam, brodimoprim, butirosin, capreomycin, carumonam, cefadroxil, cefatrizine, cefclidin, cefdinir, cefditoren, cefepime, cefetamet, cefmenoxime, cefminox, cefodizime, ceforanide, cefotaxime, cefotiam, cefozopran, cefpirome, cefprozil, cefroxadine, ceftazidime, cefteram, ceftibuten, ceftriaxone, cefuzonam, cephalexin, cephaloglycin, cephalosporin C, cephradine, clinafloxacin, colistin, cyclacillin, dapsone, diathymosulfone, dibekacinm, enviomycinm, epicillin, fortimicin(s), gentamicin(s), gramicidin S, isepamicin, kanamycin(s), lucensomycin, lymecycline, micronomicin, natamycin, neomycin, netilmicin, paromomycin, pazufloxacin, penicillin N, peplomycin, perimycin A, polymyxin, p-sulfanilylbenzylamine, ribostamycin, ristocetin, sisomicin, sparfloxacin, succisulfone, sulfachrysoidine, sulfamidochrysoidine, sulfanilic acid, sulfoxone, teicoplanin, tetroxoprim, thiazolsulfone, tigemonam, tobramycin, tosufloxacin, trimethoprim, trovafloxacin, tuberactinomycin, vancomycin and the like.

Examples of anti-fungal compounds suitable for use in the present invention include, but are not limited to azaserine, candicidin(s), mepartricin, nystatin, tubercidin and the like.

Examples of anti-neoplastic compounds suitable for use in the present invention include, but are not limited to 6-diazo-5-oxo-L-norleucine, azacitadine, azaserine, bleomycin(s), carubicin, cladribine, cytarabine, daunorubicin, denopterin, doxorubicin, edatrexate, eflornithine, epirubicin, fludarabine, gemcitabine, idarubicin, melphalan, methotrexate, mitomycin C, pirarubicin, piritrexim, pteropterin, puromycin, streptonigrin, thiamiprine, thioguanine, trimetrexate, tubercidin, ubenimex, zorubicin and the like.

Examples of immunosuppressive compounds suitable for use in the present invention include, but are not limited to gusperimus, ubenimex and the like.

Examples of local anesthetic compounds suitable for use in the present invention include, but are not limited to butethamine, naepaine, orthocaine, piridocaine and the like.

Examples of NSAID compounds suitable for use in the present invention include, but are not limited to 3-amino-4-hydroxybutyric acid, amfenac, bromfenac, mesalamine, S-adenosylmethionine and the like.

Linking Group "L"

The nature of the linking group "L" in a polymer of the invention is not critical provided the polymer of the invention possesses acceptable mechanical properties and release kinetics for the selected therapeutic application. The linking group L is typically a divalent organic radical having a molecular weight of from about 25 daltons to about 400 daltons. More preferably, L has a molecular weight of from about 40 daltons to about 200 daltons.

The linking group L typically has a length of from about 5 angstroms to about 100 angstroms using standard bond lengths and angles. More preferably, the linking group L has a length of from about 10 angstroms to about 50 angstroms.

The linking group may be biologically inactive, or may itself possess biological activity. The linking group can also comprise other functional groups (including hydroxy groups, mercapto groups, amine groups, carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

Specific and Preferred Values

Specific and preferred values listed herein for radicals, substituents, groups, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific biologically active compound that can be incorporated into the polymers of the invention is 5-aminosalicylic acid, 4-aminosalicylic acid, 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apramycin, arbekacin, aspoxicillin, aztreonam, brodimoprim, butirosin, capreomycin, carumonam, cefadroxil, cefatrizine, cefclidin, cefdinir, cefditoren, cefepime, cefetamet, cefixime, cefmenoxime, cefminox, cefodizime, ceforanide, cefotaxime, cefotiam, cefozopran, cefpirome, cefprozil, cefroxadine, ceftazidime, cefteram, ceftibuten, ceftriaxone, cefuzonam, cephalexin, cephaloglycin, cephalosporin C, cephradine, clinafloxacin, colistin, cyclacillin, dapsone, diathymosulfone, dibekacinm, enviomycinm, epicillin, fortimicin(s), gentamicin(s), gramicidin S, isepamicin, kanamycin(s), lucensomycin, lymecycline, micronomicin, natamycin, neomycin, netilmicin, paromomycin, pazufloxacin, penicillin N, peplomycin, perimycin A, polymyxin, p-sulfanilylbenzylamine, ribostamycin, ristocetin, sisomicin, sparfloxacin, succisulfone, sulfachrysoidine, sulfamidochrysoidine, sulfanilic acid, sulfoxone, teicoplanin, tetroxoprim, thiazolsulfone, tigemonam, tobramycin, tosufloxacin, trimethoprim, trovafloxacin, tuberactinomycin, vancomycin, azaserine, candicidin(s), mepartricin, nystatin, tubercidin, 6-diazo-5-oxo-L-norleucine, azacitadine, azaserine, bleomycin(s), carubicin, cladribine, cytarabine, daunorubicin, denopterin, doxorubicin, edatrexate, eflornithine, epirubicin, fludarabine, gemcitabine, idarubicin, melphalan, methotrexate, mitomycin C, pirarubicin, piritrexim, pteropterin, puromycin, streptonigrin, thiamiprine, thioguanine, trimetrexate, tubercidin, ubenimex, zorubicin, gusperimus, butethamine, naepaine, orthocaine, piridocaine, 3-amino-4-hydroxybutyric acid, amfenac, bromfenac, mesalamine, or S-adenosylmethionine.

A preferred biologically active compound suitable for incorporation into polymeric polyazo compounds of the invention is 5-aminosalicylic acid or 4-aminosalicylic acid.

Another specific value for L is a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of $(C_{1-6})$alkoxy, $(C_{3-6})$cycloalkyl, $(C_{1-6})$alkanoyl, $(C_{1-6})$alkanoyloxy, $(C_{1-6})$alkoxycarbonyl, $(C_{1-6})$alkylthio, azido, cyano, nitro, halo, hydroxy, oxo, carboxy, aryl, aryloxy, heteroaryl, and heteroaryloxy.

Another specific value for L is an amino acid.

Another specific value for L is a peptide.

Another specific value for L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—).

A more specific value for L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of $(C_{1-6})$alkoxy, $(C_{3-6})$cycloalkyl, $(C_{1-6})$alkanoyl, $(C_{1-6})$alkanoyloxy, $(C_{1-6})$alkoxycarbonyl, $(C_{1-6})$alkylthio, azido, cyano, nitro, halo, hydroxy, oxo, carboxy, aryl, aryloxy, heteroaryl, and heteroaryloxy.

Another more specific value for L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—).

Another more specific value for L is a divalent, branched or unbranched, saturated or unsaturated, hydrocarbon chain, having from 3 to 15 carbon atoms.

Another more specific value for L is a divalent, branched or unbranched, hydrocarbon chain, having from 3 to 15 carbon atoms.

A preferred value for L is a divalent, branched or unbranched, hydrocarbon chain, having from 6 to 10 carbon atoms.

A more preferred value for L is a divalent hydrocarbon chain having 7, 8, or 9 carbon atoms.

A most preferred value for L is a divalent hydrocarbon chain having 8 carbon atoms.

A specific polymer of the invention comprises one or more monomer units of formula (I):

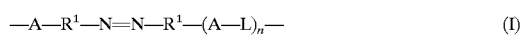

$$-A-R^1-N=N-R^1-(A-L)_n- \qquad (I)$$

and will have formula (II)

$$-(A-R^1-N=N-R^1-(A-L)_n)_x- \qquad (II)$$

wherein each $R^1$—N is a group that will provide a biologically active compound upon hydrolysis of the polymer; each A is an anhydride, an amide linkage, a thioester linkage, or an ester linkage; and L is a linking group; where n is 0 or 1 and x represents the number of repeating groups (e.g. x can be an integer from 2 to about 100, preferably from 2 to about 50, and more preferably, from 5 to 50). Suitable monomers are polymerized to provide the polyazo compounds.

Such a polymer, wherein each $R^1$ is a group that will provide a different biologically active compound upon hydrolysis of the polymer, are particularly useful for the administration of a combination of two therapeutic agents to an animal.

A preferred group of polyazo compounds includes compounds containing at least one free amine group to form the azo group and at least one free carboxylic acid group, alcohol group or amine group available for reactions which can self-polymerize or co-polymerize with carboxylic acid groups or bis(acyl) chlorides.

A specific polymeric drug delivery system for oral delivery of a drug comprises a drug incorporated in a poly(azo-anhydride).

A specific polymeric drug delivery system for oral delivery of a drug comprises a poly(azo-anyydride) where the drug is 5-ASA or 4-ASA.

A specific method of the invention is orally delivering a drug to a patient by administering to the patient the polymeric drug delivery system of a drug incorporated in a poly(azo-anhydride).

A specific method of the invention is treating intestinal conditions in a patient comprising orally administering to the patient the polymeric drug delivery system where the drug is 5-ASA or 4-ASA.

Another specific method of the invention is treating tuberculosis in a patient comprising orally administering to the patient a polymeric drug delivery system of the invention wherein the drug is 4-ASA.

Another specific method of the invention is producing oral formulations of a drug which provide for targeted drug release and controlled systemic absorption comprising incorporating a drug into a poly(azo-anhydride) compound.

Formulations

The polymers of the invention can be formulated as pharmaceutical compositions and administered to a mammalian host, such as a human patient in a variety of forms adapted to the chosen route of administration, i.e., orally or rectally. For some routes of administration, the polymer can conveniently be formulated as micronized particles.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations preferably contain at least 0.1% of polymer by weight. The percentage of the compositions and preparations may, of course, be varied and may conveniently be between about 2 to about 60% of the weight of a given unit dosage form. The amount of polymer in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Useful solid carriers include finely divided solids such as talc, clay, microcrystalline cellulose, silica, alumina and the like. Useful liquid carriers include alcohols or glycols or alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use.

Dosages

Useful dosages of the polymers can be determined by comparing their in vitro activity, and in vivo activity of the therapeutic agent in animal models. Methods for the extrapolation of effective dosages in mice, and other animals, to humans are known to the art; for example, see U.S. Pat. No. 4,938,949. Additionally, useful dosages can be determined by measuring the rate of hydrolysis for a given polymer under various physiological conditions. The amount of a polymer required for use in treatment will vary not only with the particular polymer selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The present invention also relates to methods of using compositions comprising drugs incorporated into polyazo compounds in any application wherein oral delivery of the drug is desired. The quantity of drug in the polyazo compound to be administered to a patient which is effective for the selected use can be readily determined by those of ordinary skill in the art without undue experimentation. The quantity essentially corresponds stoichiometrically to the amount of drug which is known to produce an effective treatment for the selected use.

Combination Therapies

The polymers of the invention are also useful for administering a combination of therapeutic agents to an animal. Such a combination therapy can be carried out in the following ways: 1) a second therapeutic agent can be dispersed within the polymer matrix of a polymer of the invention, and can be released upon degradation of the polymer; 2) a second therapeutic agent can be appended to a polymer of the invention (i.e. not in the backbone of the polymer) with bonds that hydrolyze to release the second therapeutic agent under physiological conditions; 3) the polymer of the invention can incorporate two therapeutic agents into the polymer backbone (e.g. a polymer comprising one or more units of formula (I)) or 4) two polymers of the invention, each with a different therapeutic agent can be administered together (or within a short period of time).

Thus, the invention also provides a pharmaceutical composition comprising a polymer of the invention and a second therapeutic agent that is dispersed within the polymer matrix of a polymer of the invention. The invention also provides a pharmaceutical composition comprising a polymer of the invention having a second therapeutic agent appended to the polymer (e.g. with bonds that will hydrolyze to release the second therapeutic agent under physiological conditions).

The polymers of the invention can also be administered in combination with other therapeutic agents that are effective to treat a given condition to provide a combination therapy. Thus, the invention also provides a method for treating a disease in a mammal comprising administering an effective amount of a combination of a polymer of the invention and another therapeutic agent. The invention also provides a pharmaceutical composition comprising a polymer of the invention, another therapeutic agent, and a pharmaceutically acceptable carrier.

Preparation of Polymers of the Invention

Processes for preparing polymers of the invention are provided as further embodiments of the invention and are illustrated by the following procedures in which the meanings of the generic radicals are as given above unless otherwise qualified.

In general, the polymers of the invention can be prepared, as illustrated in Scheme 1, from an azo containing compound, which can release a biologically active compound, of formula $(X_1—R^1—N=N—R^1—X_2)$ and a linker precursor of formula $Z_1—L—Z_2$, wherein $X_1$, $X_2$, $Z_1$, and $Z_2$ are independently selected from the values in the table below.

Scheme 1

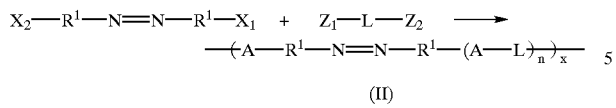

(II)

wherein n is 0 or 1; and x represents the number of repeating units.

The azo containing compound and the linker precursor can be polymerized using well known synthetic techniques (e.g. by condensation) to provide a polymer of the invention (I) wherein each $R^1$ is a group that will provide a biologically active compound upon hydrolysis of the polymer and cleavage of the azo-bond; each A is an anhydride linkage, an amide linkage, a thioester linkage, or an ester linkage; L is a linking group and n is 0 or 1.

Depending on the reactive functional group ($X_1$ or $X_2$) of the biologically active compound, a corresponding functional group ($Z_1$ or $Z_2$) can be selected from the following table, to provide an anhydride linkage, ester linkage, thioester linkage, or amide linkage in the polymer backbone.

| Functional Group On Biologically active compound ($X_1$ or $X_2$) | Functional Group On Linker Precursor ($Z_1$ or $Z_2$) | Resulting Linkage In Polymer |
|---|---|---|
| —COOH | —COOH | Anhydride |
| —COOH | —OH | Ester |
| —COOH | —NHR | Amide |
| —COOH | —SH | Thioester |
| —OH | —COOH | Ester |
| —SH | —COOH | Thioester |
| —NHR | —COOH | Amide |

As will be clear to one skilled in the art, suitable protecting groups can be used during the reaction illustrated in Scheme 1 (and in the reactions illustrated in Schemes 2-6 below). For example, other functional groups present in the biologically active compound or the linker precursor can be protected during polymerization, and the protecting groups can subsequently be removed to provide the polymer of the invention. Suitable protecting groups and methods for their incorporation and removal are well known in the art (see for example Greene, T. W.; Wutz, P. G. M. "Protecting Groups In Organic Synthesis" second edition, 1991, New York, John Wiley & sons, Inc.).

Additionally, when a carboxylic acid is reacted with a hydroxy group, a mercapto group, or an amine group to provide an ester linkage, thioester linkage, or an amide linkage, the carboxylic acid can be activated prior to the reaction, for example, by formation of the corresponding acid chloride. Numerous methods for activating carboxylic acids, and for preparing ester linkages, thioester linkages, and amide linkages, are known in the art (see for example Advanced Organic Chemistry: Reaction Mechanisms and Structure, 4 ed., Jerry March, John Wiley & Sons, pages 419–437 and 1281).

A polyester of the invention can be formed from an azo containing compound of formula (HO—$R^1$—N=N—$R^1$—OH) and from a linker precursor of formula HOOC—L—COOH as illustrated in Scheme 2.

SCHEME 2

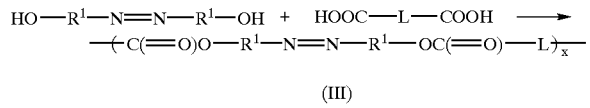

(III)

wherein x represents the number of repeating units. Reaction of the hydroxy groups of the azo containing compound with the carboxylic acids of the linker precursor provides a polymer of formula (III), which is a polymer of the invention.

A polyamide of the invention can be prepared using a procedure similar to that illustrated in Scheme 2 by replacing the biologically active dihydroxy compound in Scheme 2 with a suitable biologically active diamino compound.

A polythioester of the invention can be prepared using a procedure similar to that illustrated in Scheme 2 by replacing the biologically active dihydroxy compound in Scheme 2 with a suitable azo-dimercapto compound.

A polyester/polyamide of the invention can be formed from a biologically active compound of formula (H(R)N—$R^1$—N=N—$R^1$—OH) and from a linker precursor of formula HOOC—L—COOH as illustrated in Scheme 3.

SCHEME 3

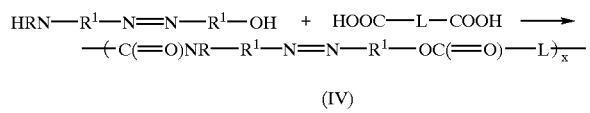

(IV)

wherein x represents the number of repeating units. Reaction of the hydroxy group and the amino group of the azo compound with the carboxylic acids of the linker precursor provides a polymer of formula (IV), which is a polymer of the invention.

Similarly, a polyester of the invention can be formed from an azo containing compound of formula (HO—$R^1$—N=N—$R^1$—COOH) and from a linker precursor of formula HOOC—L—OH as illustrated in Scheme 4.

SCHEME 4

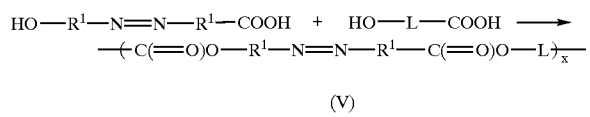

(V)

wherein x represents the number of repeating units. Reaction of the hydroxy groups with the carboxylic acid groups provides a polymer of formula (V), which is a polymer of the invention.

In Schemes I–IV, each $R^1$ is independently a group that will provide a biologically active compound upon hydrolysis of the polymer and cleavage of the azo-bond; each A is an anhydride linkage, an amide linkage, a thioester linkage, or an ester linkage; L is a linking group; n is 0 or 1; and x is 2 to about 100 (or 2 to about 50; or 5 to about 50).

Other polymers of the invention can be formed using the reactions described herein, using starting materials that have suitable groups to prepare the desired polymer.

Polymeric drug delivery systems of the present invention can be characterized by proton nuclear magnetic resonance (NMR) spectroscopy, infrared (IR) spectroscopy, gel permeation chromatography (GPC), high performance liquid chromatography (HPLC), differential scanning calorimetry (DSC), and thermal gravimetric analysis (TGA). For infrared spectroscopy, samples are prepared by solvent casting on NaCl plates. $^1$H and $^{13}$C NMR spectroscopy is obtained in solutions of $CDCl_3$ or DMSO-$d_6$ with solvent as the internal reference.

GPC is performed to determine molecular weight and polydispersity. In this method, samples are dissolved in tetrahydrofuran and eluted through a mixed bed column (PE PL gel, 5 μm mixed bed) at a flow rate of 0.5 mL/minute. It is preferred that the samples (about 5 mg/mL) be dissolved into the tetrahydrofuran and filtered using 0.5 μm PTFE syringe filters prior to column injection. Molecular weights are determined relative to narrow molecular weight polystyrene standards (Polysciences, Inc.).

Thermal analysis can also be performed using a system such as the Perkin-Elmer system consisting of a TGA 7 thermal gravimetric analyzer equipped with PE AD-4 autobalance and Pyris 1 DSC analyzer. In this system, Pyris software is used to carry out data analysis on a DEC Venturis 5100 computer. For DSC, an average sample weight of 5–10 mg is heated at 10° C./minute at a 30 psi flow of $N_2$. For TGA, an average sample weight of 10 mg is heated at 20° C./minute under a 8 psi flow of $N_2$. Sessile drop contact angle measurements are obtained with an NRL Goniometer (Rame-hart) using distilled water. Solutions of polymer in methylene chloride (10% wt/volume) are spun-coated onto glass slips, at 5,000 rpm for 30 seconds.

Degradation and drug release profiles of the polymer drug delivery systems of the present invention can also be determined routinely. For these experiments, the polymers are processed into either films, pellets, microspheres, nanospheres or fibers (depending on their properties). After processing, the materials are be characterized to determine if any physicochemical changes have occurred during processing. Uniform processed, weighed, and characterized samples are then degraded in acidic, neutral, and basic phosphate buffer (conditions chosen to simulate physiological range) in triplicate. Periodically the buffer is removed and replaced with fresh media to simulate sink conditions. The spent buffer is analyzed by HPLC to determine the cumulative release of the drug. At defined time periods, samples are removed from the buffer and superficially dried (blotted). They are then weighed to determine the water uptake. At this point, the contact angle (hydrated) is also measured to determine changes in hydrophobicity during degradation. The samples are then thoroughly dried under vacuum and weighed to determine their mass loss. Contact angles (dry) are measured again to determine the hydrophobicity of the dry material, and how it compares to that of the hydrated material. By plotting cumulative release of the degradation products over time, the degradation kinetics can be defined. For the polyazo polymers the degradation product contains an amino groups (the free drug is only obtained with enzymatic cleavage of the azo bond). Wet and dry polymer weights over time indicate if the material is bulk or surface eroding. If there is an increase in water uptake, it can be determined that the polymer is bulk eroding, whereas if there is little or no water uptake the material is considered surface-eroding. By plotting the changes in dry weight versus time, the mass lost by the polymer as it erodes can be determined. This information will give additional insight into how the material is degrading. Changes in molecular weight over time are also examined to bolster the degradation results.

Polyazo compounds used in the present invention can be isolated by known methods commonly employed in the field of synthetic polymers to produce a variety of useful products with valuable physical and chemical properties. Polymeric drug delivery systems can be readily processed into tablets, coatings, and microspheres, and may also be processed by compression molding and extrusion. In a preferred embodiment, the polyazo compounds of the present invention are incorporated into oral formulations such as tablets, capsules, or liquid suspensions.

EXAMPLE 1

The polymeric drug delivery systems of the present invention comprising 5-ASA incorporated into a polyazo compound can be prepared following Scheme 5. In Scheme 5, 5-nitrosalicylic acid is dimerized via azo linkage to form olsalazine using sodium hydroxide and zinc dust in methanol/water. Alternatively, the disodium salt of the diacid (olsalazine) can be purchased from Pharmacia-Upjohn. The azo compound is then converted to the activated monomer (bis-anhydride) by heating it at reflux in acetic anhydride. The monomer is polymerized by heating under vacuum to provide the polyazo compound where x, the number of repeating units, is from 2 to about 10.

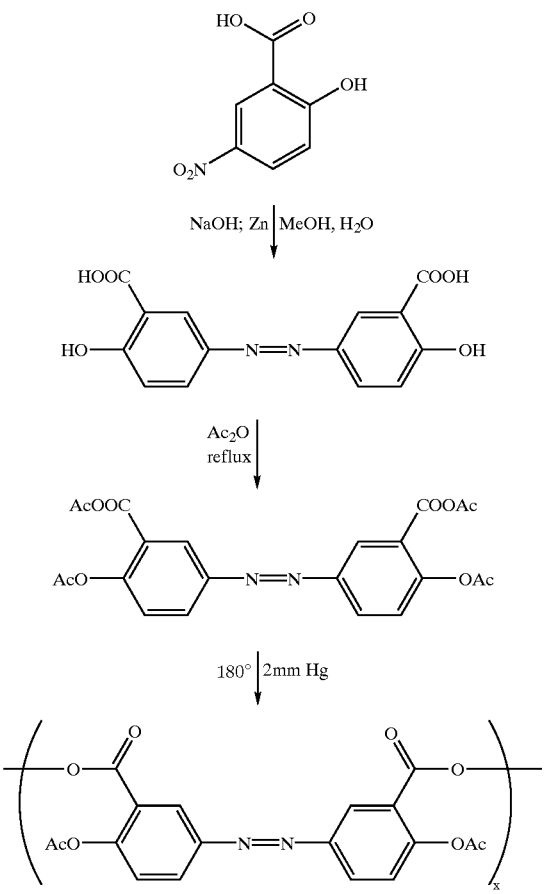

Scheme 5

EXAMPLE 2

In Example 2, Scheme 6 illustrates the synthesis of a poly(azo-anhydride) compound linking 4-ASA. The 4-aminosalicylic acid is converted to its methyl ester with sulfuric acid in methanol. Methyl-4-aminosalicylate is dimerized via azoxy linkage with hydrogen peroxide in acetic acid. The azoxy compound is reduced to the hydrazo compound with zinc dust in acetic acid. The hydrazo compound is oxidized to the azo compound with sodium perborate in acetic acid. The methyl esters are cleaved with alkali to give the prepolymer azo diacid. The diacid is converted to the activated monomer by refluxing in an excess of acetic anhydride. The monomer is then converted to the polyazo compound.

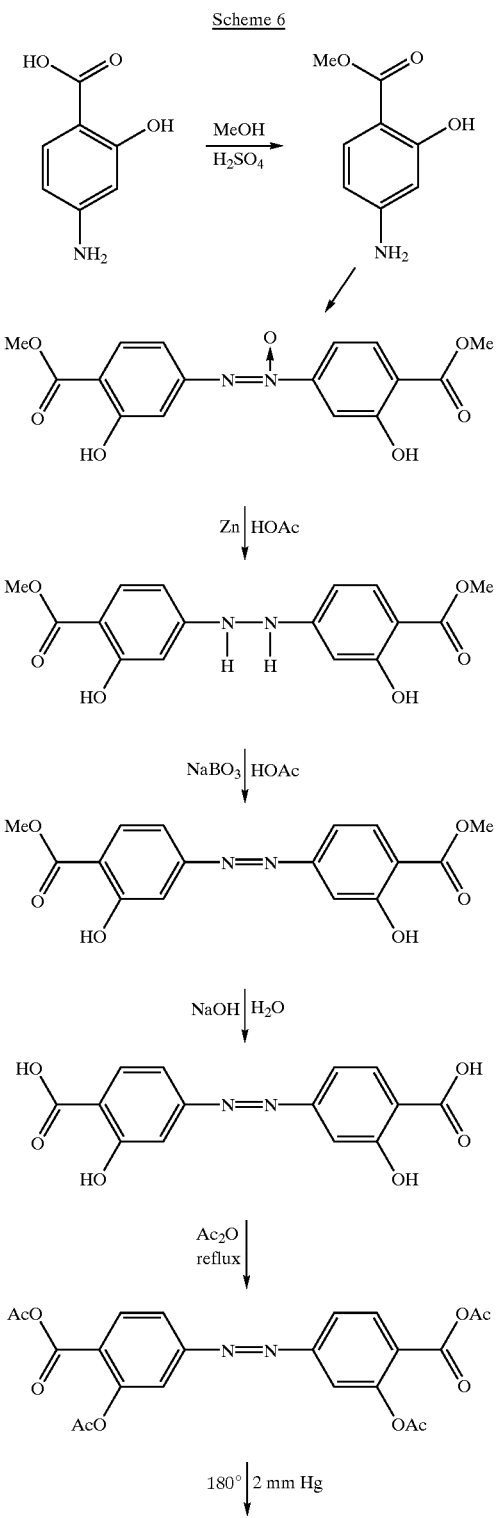

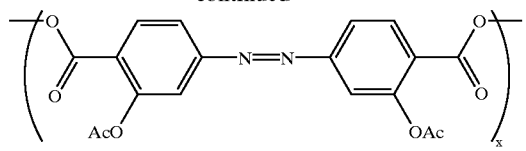

Activity

The ability of a polymer of the invention to produce a given therapeutic effect can be determined using in vitro and in vivo pharmacological models which are well known to the art.

All publications, patents, and patent documents (including the entire contents of U.S. Provisional Patent Application No. 60/220,998, filed Jul. 27, 2000) are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A polymer comprising a backbone, wherein the backbone comprises one or more azo linkages, and wherein the backbone comprises one or more groups that will yield a biologically active compound upon hydrolysis of the polymer.

2. The polymer of claim 1 which comprises one or more units of formula (I) in the backbone:

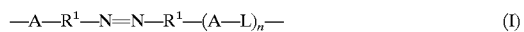

wherein
each $R^1$—N is a group that will provide a biologically active compound upon hydrolysis of the polymer;
each A is independently an anhydride linkage, an amide linkage, a thioester linkage, or an ester linkage;
L is a linking group; and n is 0 or 1.

3. The polymer of claim 1 wherein the biologically active compound is a non-steroidal anti-inflammatory drug, an anti-bacterial drug, an anti-fungal drug, an anti-cancer drug, an anti-thrombotic drug, an immunosuppressive drug, an analgesic drug or an anesthetic drug.

4. The polymer of claim 1, wherein the biologically active compound is 5-aminosalicylic acid, 4-aminosalicylic acid, 2-p-sulfanilyanilinoethanol, 4,4'-sulfinyldi-aniline, 4-sulfanilamidosalicylic acid, acediasulfone, acetosulfone, amikacin, amoxicillin, amphotericin B, ampicillin, apramycin, arbekacin, aspoxicillin, aztreonam, brodimoprim, butirosin, capreomycin, carumonam, cefadroxil, cefatrizine, cefclidin, cefdinir, cefditoren, cefepime, cefetamet, cefixime, cefmenoxime, cefminox, cefodizime, ceforanide, cefotaxime, cefotiam, cefozopran, cefpirome, cefprozil, cefroxadine, ceftazidime, cefteram, ceftibuten, ceftriaxone, cefuzonam, cephalexin, cephaloglycin, cephalosporin C, cephradine, clinafloxacin, colistin, cyclacillin, dapsone, diathymosulfone, dibekacinm, enviomycinm, epicillin, fortimicin(s), gentamicin(s), gramicidin S, isepamicin, kanamycin(s), lucensomycin, lymecycline, micronomicin, natamycin, neomycin, netilmicin, paromomycin, pazufloxacin, penicillin N, peplomycin, perimycin A, polymyxin, p-sulfanilylbenzylamine, ribostamycin, ristocetin, sisomicin, sparfloxacin, succisulfone, sulfachrysoidine, sulfamidochrysoidine, sulfanilic acid, sulfoxone, teicoplanin, tetroxoprim, thiazolsulfone, tigemonam, tobramycin, tosufloxacin, trimethoprim, trovafloxacin, tuberactinomycin, vancomycin, azaserine, candicidin(s), mepartricin, nystatin, tubercidin, 6-diazo-5-oxo-L-norleucine, azacitadine, bleomycin(s), carubicin, cladribine, cytarabine, daunorubicin, denopterin, doxorubicin, edatrexate, eflornithine, epirubicin, fludarabine, gemcitabine, idarubicin, melphalan, methotrexate, mitomycin C, pirarubicin, piritrexim, pteropterin, puromycin, streptonigrin, thiamiprine, thioguanine, trimetrexate, tubercidin, zorubicin, gusperimus, ubenimex, butethamine, naepaine, orthocaine, piridocaine, 3-amino-4-hydroxybutyric acid, amfenac, bromfenac, mesalamine, or S-adenosylmethionine.

5. The polymer of claim 4, wherein the biologically active compound is 5-aminosalicylic acid or 4-aminosalicylic acid.

6. The polymer of claim 4, wherein the biologically active compound is 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apramycin, arbekacin, aspoxicillin, aztreonam, brodimoprim, butirosin, capreomycin, carumonam, cefadroxil, cefatrizine, cefclidin, cefdinir, cefditoren, cefepime, cefetamet, cefixime, cefmenoxime, cefminox, cefodizime, ceforanide, cefotaxime, cefotiam, cefozopran, cefpirome, cefprozil, cefroxadine, ceftazidime, cefteram, ceftibuten, ceftriaxone, cefuzonam, cephalexin, cephaloglycin, cephalosporin C, cephradine, clinafloxacin, colistin, cyclacillin, dapsone, diathymosulfone, dibekacinm, enviomycinm, epicillin, fortimicin(s), gentamicin(s), gramicidin S, isepamicin, kanamycin(s), lucensomycin, lymecycline, micronomicin, natamycin, neomycin, netilmicin, paromomycin, pazufloxacin, penicillin N, peplomycin, perimycin A, polymyxin, p-sulfanilylbenzylamine, ribostamycin, ristocetin, sisomicin, sparfloxacin, succisulfone, sulfachrysoidine, sulfamidochrysoidine, sulfanilic acid, sulfoxone, teicoplanin, tetroxoprim, thiazolsulfone, tigemonam, tobramycin, tosufloxacin, trimethoprim, trovafloxacin, tuberactinomycin or vancomycin.

7. The polymer of claim 4, wherein the biologically active compound is azaserine, candicidin(s), mepartricin, nystatin, tubercidin.

8. The polymer of claim 3, wherein the biologically active compound is a non-steroidal anti-inflammatory drug.

9. The polymer of claim 8, wherein the biologically active compound is 3-amino-4-hydroxybutyric acid, amfenac, bromfenac, mesalamine or S-adenosylmethionine.

10. The polymer of claim 4, wherein the biologically active compound is 6-diazo-5-oxo-L-norleucine, azacitadine, azaserine or bleomycin, carubicin, cladribine, cytarabine, daunorubicin, denopterin, doxorubicin, edatrexate, eflornithine, epirubicin, fludarabine, gemcitabine, idarubicin, melphalan, methotrexate, mitomycin C, pirarubicin, piritrexim, pteropterin, puromycin, streptonigrin, thiamiprine, thioguanine, trimetrexate, tubercidin, ubenimex or zorubicin.

11. The polymer of claim 4, wherein the biologically active compound is gusperimus or ubenimex.

12. The polymer of claim 4, wherein the biologically active compound is butethamine, naepaine, orthocaine or piridocaine.

13. The polymer of claim 2, wherein L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of $(C_{1-6})$alkoxy, $(C_{3-6})$cycloalkyl, $(C_{1-6})$alkanoyl, $(C_{1-6})$alkanoyloxy, $(C_{1-6})$alkoxycarbonyl, $(C_{1-6})$alkylthio, azido, cyano, nitro, halo, hydroxy, oxo, carboxy, aryl, aryloxy, heteroaryl, and heteroaryloxy.

14. The polymer of claim 13, wherein L is a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of $(C_{1-6})$alkoxy, $(C_{3-6})$cycloalkyl, $(C_{1-6})$alkanoyl, $(C_{1-6})$alkanoyloxy, $(C_{1-6})$alkoxycarbonyl, $(C_{1-6})$alkylthio, azido, cyano, nitro, halo, hydroxy, oxo, carboxy, aryl, aryloxy, heteroaryl, and heteroaryloxy.

15. The polymer of claim 2, wherein L is a peptide.

16. The polymer of claim 2, wherein L is an amino acid.

17. The polymer of claim 2, wherein L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—).

18. The polymer of claim 2, wherein L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of $(C_{1-6})$alkoxy, $(C_{3-6})$cycloalkyl, $(C_{1-6})$alkanoyl, $(C_{1-6})$alkanoyloxy, $(C_{1-6})$alkoxycarbonyl, $(C_{1-6})$alkylthio, azido, cyano, nitro, halo, hydroxy, oxo, carboxy, aryl, aryloxy, heteroaryl, and heteroaryloxy.

19. The polymer of claim 2, wherein L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—).

20. The polymer of claim 2, wherein L is a divalent, branched or unbranched, saturated or unsaturated, hydrocarbon chain, having from 3 to 15 carbon atoms.

21. The polymer of claim 2, wherein L is a divalent, branched or unbranched, hydrocarbon chain, having from 3 to 15 carbon atoms.

22. The polymer of claim 2, wherein L is a divalent, branched or unbranched, hydrocarbon chain, having from 6 to 10 carbon atoms.

23. The polymer of claim 2, wherein L is a divalent hydrocarbon chain having 7, 8, or 9 carbon atoms.

24. The polymer of claim 2, wherein L is a divalent hydrocarbon chain having 8 carbon atoms.

25. The polymer of claim 1, further comprising another therapeutic agent dispersed in the matrix of the polymer.

26. The polymer of claim 1, further comprising another therapeutic agent appended to the polymer backbone.

27. A pharmaceutical composition comprising a polymer of claim 1 and a pharmaceutically acceptable carrier.

28. A therapeutic method for treating a disease in an animal comprising administering to an animal in need of such therapy, an effective amount of a polymer of claim 1.

29. A therapeutic method for producing an anti-inflammatory effect in an animal comprising administering to an animal in need of such therapy, an effective amount of a polymer of claim 8.

30. A method for producing a polymer as described in claim 1 comprising co-polymerizing a compound, of formula (X$_1$—R$^1$—N=N—R$^1$—X$_2$)

and a linker precursor of formula

Z$_1$—L—Z$_2$, wherein each R$^1$ is independently a group that will provide a biologically active compound upon hydrolysis of the polymer and cleavage of the azo-bond;
L is a linking group; and
each of X$_1$, X$_2$, Z$_1$, and Z$_2$ is selected to provide an anhydride linkage, an amide linkage, a thioester linkage, or an ester linkage upon polymerization.

31. A method of delivering a biologically active compound to a host comprising administering to the host a biocompatible and biodegradable polyester or polyamide of claim 1.

32. A method for treating inflammatory bowel disease in a mammal comprising administering to the mammal in need of such therapy, an effective amount of a biocompatible and biodegradable polyanhydride polymer of claim 1.

33. A therapeutic method for treating inflammatory bowel disease comprising administering to a mammal in need of such therapy, an effective amount of a biocompatible and biodegradable polyanhydride having repeating units of the formula:

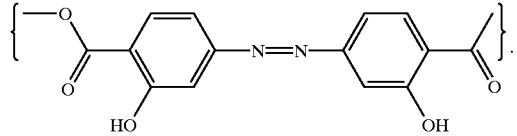

34. A polymer having repeating units of the formula:

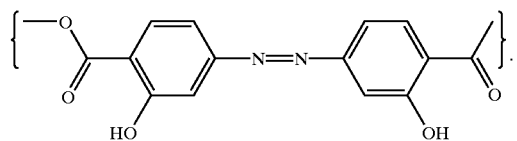

35. A therapeutic method for treating inflammatory bowel disease comprising administering to a mammal in need of such therapy, an effective amount of a biocompatible and biodegradable polyanhydride having repeating units of the formula:

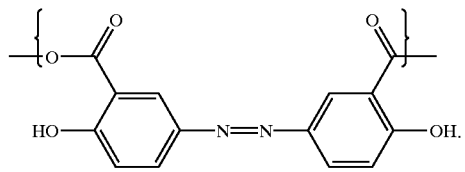

36. A polymer having repeating units of the formula:

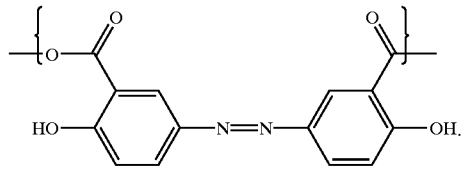

* * * * *

UNITED STATES PATENT AND TRADEMARK OFFICE
CERTIFICATE OF CORRECTION

PATENT NO. : 6,602,915 B2  Page 1 of 1
DATED : August 5, 2003
INVENTOR(S) : Kathryn E. Uhrich It is certified that error appears in the above-identified patent and that said Letters Patent is hereby corrected as shown below:

Title page,
Item [56], References Cited, U.S. PATENT DOCUMENTS, delete "Frechet et al." and insert -- Fretchet et al. -- therefor.
FOREIGN PATENT DOCUMENTS, insert -- ………….. A61K -- after "4/2001".

Column 18,
Lines 3, 12 and 31, delete "$(C_{1-6})$" before "alkoxy," and insert -- $(C_1-C_6)$ -- therefor.
Lines 3, 12 and 31, delete "$(C_{3-6})$" before "cycloalkyl," and insert -- $(C_3-C_6)$ -- therefor.
Lines 3, 12 and 31, delete "$(C_{1-6})$" before "alkanoyl," and insert -- $(C_1-C_6)$ -- therefor.
Lines 3, 12 and 31, delete "$(C_{1-6})$" before "alkanoyloxy," and insert -- $(C_1-C_6)$ -- therefor.
Lines 4, 13 and 32, delete "$(C_{1-6})$" before "alkylthio," and insert -- $(C_1-C_6)$ -- therefor.
Lines 13 and 32, delete "$(C_{1-6})$" before "alkoxycarbonyl," and insert -- $(C_1-C_6)$ -- therefor.

Signed and Sealed this

Eighth Day of June, 2004

JON W. DUDAS
*Acting Director of the United States Patent and Trademark Office*